United States Patent [19]

De Thomas et al.

[11] Patent Number: 4,885,411
[45] Date of Patent: Dec. 5, 1989

[54] HYDROGENATION PROCESS FOR CONVERTING LACTONES TO DIOLS

[75] Inventors: Waldo De Thomas, Parsippany; Paul D. Taylor, West Milford, both of N.J.

[73] Assignee: GAF Corporation, Wayne, N.J.

[21] Appl. No.: 234,354

[22] Filed: Aug. 19, 1988

Related U.S. Application Data

[62] Division of Ser. No. 126,065, Nov. 27, 1987, Pat. No. 4,797,382.

[51] Int. Cl.$^4$ .......................................... C07C 29/136
[52] U.S. Cl. .................................................... 568/864
[58] Field of Search ........................ 568/864; 502/245

[56] References Cited

U.S. PATENT DOCUMENTS

| | | | |
|---|---|---|---|
| 4,301,077 | 11/1981 | Pesa et al. | 568/864 |
| 4,377,643 | 3/1983 | Pesa et al. | 502/245 |
| 4,497,908 | 2/1985 | Lewis et al. | 502/245 |
| 4,567,160 | 1/1986 | Nay et al. | 502/326 |

*Primary Examiner*—Donald B. Moyer
*Assistant Examiner*—Karen E. Plue
*Attorney, Agent, or Firm*—Marilyn J. Maue

[57] ABSTRACT

The invention relates to a novel supported catalyst comprising (a) copper, (b) a metal having an atomic weight greater than 100 and selected from Groups VIIB and VIII of the Periodic Table and (c) an alkali metal in a weight ratio of about 8-40:0.05-5:1.5-10 and to the use of the catalyst in the hydrogenation of butyrolactone to 1,4-butanediol.

15 Claims, No Drawings

HYDROGENATION PROCESS FOR CONVERTING LACTONES TO DIOLS

This is a division of application Ser. No. 126,065, filed Nov. 27, 1987.

In one aspect the invention relates to a novel hydrogenation catalyst and to a method for its preparation.

In another aspect the invention relates to the use of said catalyst in the selective hydrogenation of a lactone to a glycol.

BACKGROUND OF THE INVENTION

Many processes for the catalytic production of glycols from lactones have been developed. Among the glycols in high demand are those having four or more carbon atoms such as 1,6-hexanediol and especially, 1,4-butanediol.

Glycols such as 1,4-butanediol and 1,6-hexanediol are useful as monomers in a number of polymers including, thermoplastics such as the polyester thermoplastics and polyether thermoplastics. Examples of such thermoplastics include poly(1,4-butylene terephthalate) resin block copolymers containing blocks of poly(butyl ether) and aliphatic polyesters such as poly(hexylene adipate).

Particularly, 1,4-butanediol may be produced by a number of processes, among which is the production in a single hydrogenation step from a diester of maleic acid or in a two step process converting maleic anhydride first to gamma-butyrolactone and subsequently in a second reaction step to 1,4-butanediol. Several references have dealt with the conversion of gamma-butyrolactone to 1,4-butanediol, the majority of which recommend the liquid phase for carrying out the reaction. However, it is known to conduct the reaction in the vapor phase as well.

WO No. 82/03854, Bradley, et al., discloses the hydrogenolysis of gamma-butyrolactone in the vapor phase over a copper oxide and zinc oxide catalyst. Reactor productivity in this process is generally low.

British Patent No. 1,230,276 discloses the hydrogenation of gamma-butyrolactone using a copper oxide-chromium oxide catalyst. The hydrogenation is carried out in the liquid phase. Batch reactions are exemplified having very high total reactor pressures. Reactant and product partial pressures in the reactors are well above the respective dew points.

British Patent No. 1,314,126 and U. S. Patent No. 4,652,685 discloses the hydrogenation of gamma-butyrolactone in the liquid phase over a nickel-cobalt-thorium oxide catalyst. Batch reactions are exemplified having high total pressures and component partial pressures well above respective component dew points. Like the process above, this catalytic reaction is time consuming and expensive to operate.

British Patent No. 1,344,557 and U.S. Patent No. 4,652,685 discloses the hydrogenation of gamma-butyrolactone in the liquid phase over a copper oxide-chromium oxide catalyst. A vapor phase or vapor containing mixed phase is indicated as suitable in some instances. A continuous flow tubular reactor is exemplified using high total reactor pressures. The selectivity of these processes is not entirely satisfactory due in part to the moderate activity of the catalyst.

British Patent No. 1,512,751 discloses the hydrogenation of gamma-butyrolactone to 1,4-butanediol in the liquid phase over a copper oxide-chromium oxide catalyst. Batch reactions are exampified with high total reactor pressures and, where determinable, reactant and product partial pressures well above the respective dew points. However the process suffers the same objections pointed out above.

U.S. Pat. No. 4,301,077 discloses the hydrogenation to 1,4-butanediol of gamma-butyrolactone over a Ru-Ni-Co-Zn catalyst. As taught, the reaction may be conducted in the liquid or gas phase or in a mixed liquid-gas phase. Exemplified are continuous flow liquid phase reactions at high total reactor pressures and relatively low reactor productivities.

U.S. Pat. ent No. 4,048,196 discloses the production of 1,4-butanediol by the liquid phase hydrogenation of gamma-butyrolactone over a copper oxide-zinc oxide catalyst. Exemplified is a continuous flow tubular reactor operating at high total reactor pressures and high reactant and product partial pressures.

While the process of the above references are convenient to produce small quantities of 1,4-butanediol, on scale-up, it is discovered that generally low reactor productivities necessitate large reactors to produce commercial quantities. Such large reactors are impractical using the high pressures of the prior art references.

Accordingly, it is an object of the present invention to overcome the above deficiencies and to produce glycols from lactones, and in particular, 1,4-butanediol from gamma-butyrolactone in high yield and selectivity.

It is another object of the present invention to markedly increase reactor productivity in the hydrogenation of lactones to diols.

It is another object of the present invention to provide a highly active catalyst for improved diol selectivity which catalyst can be prepared by an economical and commerically feasible process.

These and other objects of the invention will become apparent from the following description and disclosure.

THE INVENTION

In accordance with this invention there is provided a highly active hydrogenation catalyst of (a) between about 8 and about 40 wt. % copper; (b) between about 0.05 and about 5 wt. % of a metal having an atomic weight greater than 100 and selected from Groups VIIB and VIII of the Periodic Table and (c) between about 1.5 and about 10 wt. % of an alkali metal; the preferred weight ratio ranges being between about 10 and about 25wt. % of component (a) between about 0.09 and about 1 wt. % of component (b) and between about 2 and about 6 wt. % of component (c). The remaining amount of the catalyst, composition, e.g. about 45% to about 97% of the composition, represents the support on which the metals are deposited. Suitable supports include magnesium silicate, silica, alumina and magnesium oxide-silicon oxide mixtures. The alkali metal can be either an alkali earth metal or an alkaline metal, preferably potassium, sodium, calcium or lithium or mixtures of these. Most preferred of these metal species are potassium and sodium.

The metals which comprise component (b) are selected from the group of palladium, platinum, rhodium, ruthenium, rhenium, osmium and iridium and mixtures thereof; of these palladium or mixtures containing palladium are preferred.

The catalytic materials of the present invention are conveniently prepared by mixing the nitrate, acetate, carbonate or chloride salts of copper and component (b)

with an alkali earth metal or alkaline metal base, such as the hydroxides or aluminates of the alkali metal in aqueous solution, e.g. a 40% to 80% aqueous solution, in proportions suitable to provide the metal ratio within the above range. Generally, the weight ratio of copper salt to the salt of component (b) is between about 20:1 and about 500:1. The weight ratio of the salt of component (b) to alkali metal compound is between about 1:15 and about 1:1. These components are mixed at ambient temperature and pressure until a homogeneous distribution is attained. The insoluble support material, in particulate form, is then added to the solution and uniformly mixed therein to form a slurry. In cases where the salts of copper and component (b) are other than carbonates, an alkaline metal carbonate is then added to precipitate carbonate salts of these metals with absorbed alkali metal onto the support material. The slurry is agitated until the required amount of active ingredients have been deposited on the support, after which the solids are recovered by filtration or liquid decantation as a wet cake which is then dried and calcined to convert the carbonate salts to oxides. Calcination is generally effected at a temperature of between about 350° C. and about 475° C. for a period of from about 10 to about 20 hours. The product is recovered in discrete particles such as granules, dust or powder which can be formed into tablets, hollow or solid core extruded fluted shapes or any other convenient form. The metal salts can be deposited on the support sequentially with drying and calcining between each addition if desired for closer control of the catalyst composition. Sintering of the catalyst is to be avoided; accordingly, the upper calcination temperature is critical for maintaining high catalyst activity.

The catalyst prepared in the above manner, is then reduced for suitable use in the hydrogenation of lactones to the selective production of glycols. To prevent reversion of metallic copper, palladium and alkali metal to oxides, it is preferred that the reduction of catalyst oxides be effected imminent to use in the high temperature hydrogenation of lactone or reduced in situ in the hydrogenation reaction. The catalyst reduction is efficiently carried out under relatively mild conditions, between about 150° C. and about 350° C., over a period of from about 5 to about 12 hours by contacting the supported metal oxides with gradually increasing amounts of hydrogen at incrementally increasing temperatures. Since the reaction is highly exothermic, heat in the reduction zone is controlled by initial dilution of the hydrogen with an inert gas such as nitrogene, helium, argon, neon, etc. Initial contact with reducing gas can be effected with as little as 0.5% hydrogen in nitrogen diluent at a temperature of between about 175° and about 210° C.; although hydrogen dilution to between 0.5% and 10% for initial contact is effective. Generally, the higher the concentration of the copper component, the greater the dilution of hydrogen to control the exotherm. In a preferred embodiment, after about 0.5 to about 2 hours contact with 1% hydrogen at about 180°–200° C., the hydrogen concentration is increased and the temperature is raised to about 250° C. where it is held for an additional 0.5 to 2 hours. Finally, the temperature is raised to 300° C. and the solids contacted with hydrogen for an additional 4 to 8 hours until substantially all of the metal oxides and alkali metal are converted to the metallic state. During this operation, the concentration of hydrogen is gradually increased to 100% and the oxides are decomposed to leave metallic copper, the metal or metals of component (b) and alkali metal absorbed on the support. Catalysts generally having a surface area of from about 10 to about 250 m²/g are suitably employed, although those having a surface area of from about 30 to about 150 m²/g and a pore volume of from about 0.2 to about 1.2 cm³/g are most preferred. The catalyst in this reduced state is then suitably introduced into the hydrogenation zone for conversion of the lactone to a glycol.

The lactones suitably employed in the process using the present catalyst are represented by the formula:

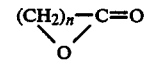

wherein n is an integer having a value of from 3 to 8 of which butyrolactone, valerolactone, caprolactone and capylolactone are preferred species; butyrolactone being most preferred. Lactones wherein one or more of the methylene groups are substituted with lower alkyl, e.g., 3-methyl-butyrolactone, 4-ethyl-butyrolactone, 3,4-dimethyl-butyrolactone, 4-methyl-valerolactone, 4-methyl-caprolactone, etc. are also suitably employed.

In a particular embodiment of this invention, butyrolactone and hydrogen are reacted in the vapor phase in a catalyst fixed bed tubular reactor to the corresponding 1,4-butanediol. The mole ratio of hydrogen to lactone can be varied between about 50:1 and about 300:1, however, a ratio of 100:1 to 200:1 is preferred. In a continuous operation, grams of reactant feed/hour/grams of catalyst is between about 0.05 to about 0.2, or 1 gram of feed per hour to 20 grams of catalyst in the fixed bed operation. The pH of the reaction should be maintained on the alkaline side, for example at a pH of between about 7.5 and about 10. The reaction is effected above the dew point of the lactone reactant, which, in the case of butyrolactone, is above 100° C. Generally, the reaction temperature is maintained between about 140° C. and 250° C., preferably, between about 160° C. and about 180° C. The hydrogen pressure in the vapor phase reaction may vary between about 100 and about 1500 pounds, preferably, between about 400 and about 1,000 pounds. It is found in the hydrogenation of lactone that the lower temperature favors selectivity but results in lower conversions. The ideal temperature and pressure for conversion of butyrolactone has been found to be about 165°–175° C. at about 600–900 pounds hydrogen.

The resulting product vapors are condensed to give product in at least 85% yield ad up to 97% purity. The presence of contaminants such as tetrahydrofuran and butanol are reduced to less than 1% by the use of the present catalyst system.

The present catalytic reactions of lactones to diols can be carried out in the vapor or in the liquid phase and in a batch or continuous manner. In the liquid phase somewhat lower temperatures and higher pressures can be employed. For example, temperatures between about 130° C. and about 160° C. and pressure between about 500 and about 1500 pounds hydrogen, preferably 600 to 1200 pounds hydrogen, are suitable.

In both liquid and vapor phase reactions, the use of a diluent is optional. When employed in vapor phase the diluent such as an alcohol, ether, hydrocarbon should have a boiling point below the operating temperature; whereas in liquid phase reactions diluents having a boiling point above operating temperature are employed.

Among the liquid compounds which may be used as diluents in the liquid phase reaction are high boiling alcohols, such as dodecanol, ethylene glycol, high boiling ethers, water, N-alkylpyrrolidones, such as N-methyl-2-pyrrolidone, butanediol, and the like. Dilution of the reactants may be as high as 50%, although the diluent concentration of not more than 35% is preferred.

In a batch operation, between about 1 wt. % and about 5 wt. % catalyst with respect to lactone is employed. Product yields up to about 99% in 99% purity are obtainable by the use of the present catalyst.

Preparations for 1,6-hexanediol and other diols such as 1,5-pentanediol, 1,7-heptanediol, 1,8-octanediol from their corresponding lactones are effected similar to the procedure described above for the conversion of butyrolactone to butanediol.

Having thus generally described the invention reference is now made to the following Examples which illustrate preferred embodiments of the invention but which are not to be construed as unduly limiting to the scope which is discussed above and defined in the appended claims.

EXAMPLES 1

CATALYST PREPARATION

To a solution of 23.0 g. copper nitrate, 0.15 g. of palladium nitrate and 3.0g of potassium hydroxide in 55 ml of water was added 42 g. of magnesium silicate granules (8 mesh). The slurry was stirred at room temperature for one hour to allow the salt solution to be absorbed by the granules. The excess liquid was decanted and the catalyst dried in a vacuum oven at 50° C. and 80 mm Hg vacuum for 2 hours. The decanted liquid salt solution was added to the dried catalyst for additional absorbtion. After all of the salt solution was absorbed, the catalyst was dried at 50° C. in a vacuum oven, and then calcined at 400° C. for 15 hours. The granular catalytic product contained 12% Cu, 0.1% Pd and 5% KOH.

EXAMPLE 2

USE OF CATALYST IN HYDROGENATION REACTION

A stainless steel tubular reaction with an O.D. of 1 inch and I.D. 0.93 inches was packed with 70 ml (27 g.) of the catalyst from Example 1 to provide a 7 inch bed length. The catalyst was reduced over a six hour period at 150°–300° C. using hydrogen in nitrogen in increasing concentration of from about 3% to about 10% $H_2$. The hydrogen mixture was introduced intermittently until there was little exotherm, after which the hydrogen concentration was increased to 100%. A feed of $\gamma$-Butyrolactone was pumped to a vaporizer from which the vapor was carried by a hydrogen stream to the reaction. The ratio of hydrogen to butyrolactone feed (99% pure) was 150:1. The reactor was maintained at 160° C. temperature, 600 psig. pressure and an LHSV of 0.05 (g. of feed/hour/volume of catalyst). The product vapors were collected and condensed. A conversion of 90% butyrolactone with 95% selectivity to butanediol was obtained.

EXAMPLE 3

Example 1 was repeated, except that the amount of palladium nitrate was increased to 0.3 g. and the amount of potassium hydroxide was decreased to 1.2 g. The resulting catalyst contained 12% metallic copper, 0.5% metallic palladium and 2% KOH.

Example 2 was repeated using this catalyst, except that the hydrogen pressure was maintained at 900 psig. and the LHSV was 0.12. A 96.5% conversion of butyrolactone with 99.0% selectivity to butanediol was obtained.

EXAMPLE 4

Example 1 was repeated, except that the amount of palladium nitrate was increased to 0.45 g. and the amount of potassium hydroxide was reduced to 1.8 g. The resulting catalyst contained 12% metallic copper, 0.3% metallic palladium and 3% KOH.

Example 2 was repeated using this catalyst, except that the hydrogen pressure was maintained at 900 psig. A 95% conversion of butyrolactone with 99% selectivity to butanediol was obtained.

EXAMPLE 5

Example 1 was repeated, except that the amount of palladium nitrate was increased to 0.3 g. and the amount of potassium hydroxide was decreased to 1.8 g. The resulting catalytic product contained 12% metallic copper, 0.2% metallic palladium and 3% KOH.

Example 2 was repeated using the catalyst of this example, except that the hydrogenation temperature employed was 180° C. and the LHSV was 0.06. An 85% conversion of butyrolactone with 96% selectivity to butanediol was obtained.

EXAMPLE 6

Example 1 was repeated, except that the amount of copper nitrate was increased to 28.7 g., palladium nitrate was increased to 0.45 g., and the amount of potassium hydroxide was decreased to 1.8 g. The resulting catalyst contained 15% metallic copper, 0.3% metallic palladium and 3% KOH.

Example 2 was repeated using the catalyst, except that $\gamma$-caprolactum was substituted for butyrolactam and the hydrogenation temperature was maintained at 180° C. A 92% conversion of $\gamma$-caprolactam with 92% selectivity to hexanediol was obtained.

EXAMPLE 7

Example 1 was repeated, except that the amount of palladium nitrate was increased to 0.45 g. and the amount of potassium hydroxide was reduced to 1.2 g. The resulting catalyst contained 12% metallic copper, 0.3% metallic palladium and 2% KOH.

Example 2 was repeated using this catalyst, except that the liquid feed to the vaporizer was a 1:1 mixture of butyrolactone and 1,4-butanediol, the hydrogen pressure was maintained at 900 psig. and the LHSV was 0.1. A 98% conversation of butyrolactone with 97% selectivity to butanediol was obtained.

EXAMPLE 8

Example 1 is repeated, except that a $\gamma$-alumina support is substituted for magnesium silicate and sodium hydroxide is substituted for potassium hydroxide. The catalyst product contains 12% metallic copper, 0.1% metallic palladium and 5% NaOH supported on $\gamma$-alumina.

The procedure described in Example 2 is repeated with this catalyst and a 90% conversion of butyrolactone with 90% selectivity to butanediol is obtained.

When the other granular support materials, e.g., silica alumina, silica, etc. are substituted in Example 1 for magnesium silicate the conversion of butyrolactone and selectivity to butanediol are similar.

Also any of the other above named lactones can be substituted for butyrolactone in the hydrogenation reaction where the temperature is maintained above the dew point of the lactone, to provide at least 85% conversion of lactone in high selectivity to diol product.

EXAMPLE 9

Example 1 is repeated, except that the amount of copper nitrate was increased to 28.7 g. and palladium nitrate was increased to 0.45 g. The resulting catalyst contained 15% of metallic copper, 0.3% of metallic palladium and 5% of KOH.

This catalyst was used in the liquid phase hydrogenation of butyrolactone to butanediol. The hydrogenation reaction was conducted at 140° C. and under 1200 psig. hydrogen pressure, by means of hydrogen to butyrolactone feed mole ratio of 100:1, in order to maintain the butyrolactone in the liquid phase. The procedure in the tubular reaction and catalyst bed described in Example 2 was repeated except that the LHSV was raised to 0.1. The liquid diol product was cooled and collected. A conversion of 99% butyrolactone with 93% selectivity to butanediol was realized.

EXAMPLE 10

Example 1 is repeated except the the amount of palladium nitrate was increased to 0.45 g. and a 1/16 inch extruded and fluted magnesium silicate support is substituted for the magnesium silicate granules. The resulting catalyst contained 12% of metallic copper, 0.3% metallic palladium and 5% KOH on the support in an extruded, fluted form.

The hydrogenation reaction of butyrolactone as described in Example 9 was repeated with the above extruded, fluted catalyst and achieves 99% conversion of butyrolactone with 94% selectivity to butanediol product.

It is to be understood that the above examples are provided to illustrate specific and preferred embodiments of the invention and that many modifications and alterations can be made in these examples which are within the scope of this invention. For example, the amounts of the metallic components of the catalyst can be widely varied within the above ranges and other metals or mixtures of metals described for components (b) in the form of their corresponding salts can be substituted in the above examples to provide comparable hydrogenation catalysts for many reactions which include the hydrogenation of esters to alcohols or aldehydes to alcohols, etc.

What is claimed is:

1. The vapor phase process of contacting a lactone having the formula:

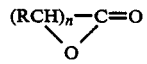

wherein n is an integer having a value of from 3 to 8 and R in each instance is hydrogen or lower alkyl, with hydrogen in a mole ratio of hydrogen to lacetone of from about 50:1 to about 300:1 in the presence of an effective catalytic amount of a supported hydrogenation catalyst consisting essentially of:
    (a) between about 8 and about 40 wt. % of metallic copper;
    (b) between about 0.05 and about 5 wt. % of palladium or a mixture of palladium with another metal having an atomic weight greater than 100 and selected from group VIIB and VIII of the Periodic Table and
    (c) between about 1.5 and about 10 wt. % of an alkali metal or an alkaline earth metal and reacting said lactone with hydrogen under alkaline conditions at a temperature above the dew point of said lactone, under a hydrogen pressure of from about 100 to about 1500 pounds to convert said lactone to the corresponding diol.

2. The process of claim 1 wherein said lactone is butyrolactone and said diol is butanediol.

3. The process of claim 1 wherein said lactone is caprolactone and said diol is hexanediol.

4. The process of claim 1 wherein the process is effected in a continuous manner in a fixed bed reactor at a rate of from about 0.05 to about 0.2 based on grams of lactone feed/hour/weight charge of catalyst.

5. The process of claim 4 wherein said lactone is butyrolactone, the catalyst is a magnesium silicate supported catalyst having from about 10% to about 25 wt. % metallic copper, from about 2 to about 6 wt. % absorbed alkali metal and between about 0.1 and about 1 wt. % palladium deposited thereon, the reaction is effected at a temperature of between about 160° C. and about 180° C. under from about 400 to about 1000 pounds hydrogen pressure and the diol is butanediol.

6. The process of claim 1 wherein the reactants are diluted with up to 50 wt. % of an inert low boiling liquid selected from the group of alcohols, including the, diol product ethers and water.

7. The process of claim 1 wherein the catalyst is present in the reaction zone in an amount between about 1 wt. % and about 5 wt. % with respect to said lactone.

8. The liquid phase process of contacting a lactone having the formula

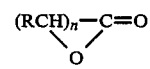

wherein n is an integer having a value of from 3 to 8 and R in each instance is hydrogen or lower alkyl, with hydrogen in a mole ratio of hydrogen to lacetone of from about 50:1 to about 300:1 in the presence of an effective catalytic amount of a supported hydrogenation catalyst consisting essentially of
    (a) between about 8 and about 40 wt. % of metallic copper;
    (b) between about 0.05 and about 5 wt. % of palladium or a mixture of palladium with another metal having an atomic weight greater than 100 and selected from group VIIB and VIII of the Periodi c Table and
    (c) between about 1.5 and abut 10 wt. % of an alkali metal or an alkaline earth metal and reacting said lacton ewith hydrogen under alkaline conditions at a temperature below the dew point of said lactone and under a hydrogen pressure of from about 500 to about 1500 pounds to convert said lactone to the corresponding diol.

9. The process of claim 8 wherein said lactone is butyrolactone and said diol is butanediol.

10. The process of claim 8 wherein said lactone is caprolactone and said diol is hexanediol.

11. The process of contacting a lactone having the formula:

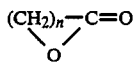

wherein n is an integer having a value of from 3 to 8, dissolved in from about 0% to about 50% of an inert solvent in the liquid phase with hydrogen in a mole ratio of hydrogen to lacetone of from about 100:1 to about 200:1 in the presence of an effective catalytic amount of supported hydrogenation catalyst consisting essentially of
  (a) between about 8 and about 40 wt. % of metallic copper;
  (b) between about 0.05 and about 5 wt. % of palladium or a mixture of palladium with another metal having an atomic weight greater than 100 and selected from group VIIB and VIII of the Periodic Table and
  (c) between about 1.5 and about 10 wt. % of an alkali metal or an alkaline earth metal and reacting said lactone with hydrogen
Table and under alkaline conditions at a temperature of between about 130° C. and about 160° C. under a hydrogen pressure of from about 600 to about 1200 pounds to convert said lactone to the corresponding diol.

12. The process of claim 8 wherein the reactants are diluted with up to 50 wt. % of an inert high boiling liquid selected from the group of high boiling alcohols, ethers, and N-alkyl pyrrolidone.

13. The process of claim 1 wherein said catalyst is support on magnesium silicate.

14. The process of claim 13 wherein said magnesium silicate is employed in an amount of between about 45% and about 97% of the total catalyst composition.

15. The process of claim 1 wherein said catalyst is in an extruded fluted form.

* * * * *